(12) United States Patent
Boughner (10) Patent No.: US 11,826,561 B2
(45) Date of Patent: Nov. 28, 2023

(54) BURR HOLE DEVICE INSERTION TOOL

(71) Applicant: Medtronic, Inc., Minneapolis, MN (US)

(72) Inventor: Kyle J. Boughner, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 134 days.

(21) Appl. No.: 17/086,794

(22) Filed: Nov. 2, 2020

(65) Prior Publication Data
US 2022/0134090 A1 May 5, 2022

(51) Int. Cl.
*A61N 1/05* (2006.01)
*A61N 1/36* (2006.01)
*A61B 90/10* (2016.01)

(52) U.S. Cl.
CPC ...... *A61N 1/0539* (2013.01); *A61B 2090/103* (2016.02); *A61N 1/0534* (2013.01); *A61N 1/3605* (2013.01)

(58) Field of Classification Search
CPC .......... A61N 1/0539; A61B 2090/103
See application file for complete search history.

(56) References Cited

U.S. PATENT DOCUMENTS

| | | | |
|---|---|---|---|
| 5,865,842 A * | 2/1999 | Knuth | A61B 5/6864 607/116 |
| 7,766,922 B1 * | 8/2010 | Daglow | A61B 90/10 606/129 |
| 10,980,978 B2 | 4/2021 | Goetz et al. | |
| 2004/0034367 A1 * | 2/2004 | Malinowski | A61B 90/11 606/129 |
| 2009/0112327 A1 * | 4/2009 | Lane | A61B 90/10 623/16.11 |
| 2011/0034981 A1 * | 2/2011 | Schulte | A61N 1/0539 607/116 |
| 2012/0277670 A1 | 11/2012 | Goetz et al. | |
| 2013/0304216 A1 * | 11/2013 | Paspa | A61N 1/0539 623/17.19 |
| 2019/0069927 A1 | 3/2019 | Baxter, III et al. | |
| 2019/0308025 A1 * | 10/2019 | Bauer | A61B 17/3468 |

* cited by examiner

*Primary Examiner* — Eric D. Bertram
(74) *Attorney, Agent, or Firm* — Shumaker & Sieffert, P.A.

(57) ABSTRACT

A system comprises a hand-held burr hole device insertion tool having a first end and a second end, the first end configured for simultaneous application of a normal force to two or more attachment points of a burr hole device component is disclosed.

18 Claims, 7 Drawing Sheets

BURR HOLE DEVICE INSERTION TOOL

TECHNICAL FIELD

The disclosure relates to burr hole tools.

BACKGROUND

In some medical systems, a lead (e.g., a lead or a catheter) is implanted in a brain of a patient. The lead may be implanted in the brain through a burr hole formed through the patient's skull. A burr hole cap assembly, which is positioned within the burr hole, may be used to retain the position of the lead relative to the burr hole, as well as substantially plug the burr hole. For instance, a burr hole cap assembly may include a base configured to be positioned in the burr hole, and a support clip configured to retain the lead and attach the lead to the burr hole cap assembly.

SUMMARY

This disclosure relates to a burr hole device insertion tool. A burr hole device insertion tool may be used by a practitioner to position a component of a burr hole cap assembly, such as a support clip, in or near a burr hole in a patient's skull. Some burr hole cap insertion tools attach to a feature located on one side of the burr hole cap, which may result in uneven distribution of pressure during insertion. Such uneven distribution of pressure may be undesirable, particularly when the burr hole device insertion tool is used to insert a support clip.

In accordance with one or more aspects of this disclosure, a burr hole cap insertion tool may be configured to simultaneously engage with a support clip at multiple locations so as to evenly distribute a pressure load to the support clip (e.g., when inserting the support clip into a base of a burr hole cap assembly). The support clip may fix the lead (or catheter) in the burr hole cap assembly. As such, distributing the pressure load evenly to the support clip during insertion of the support clip to the burr cap assembly base may reduce lead and/or catheter misplacement and/or misalignment during cap assembly.

In one example, a system comprises a hand-held burr hole device insertion tool having a first end and a second end, the first end configured for simultaneous application of a normal force to two or more attachment points of a burr hole device component.

In another example, a method comprises applying, via a hand-held burr hole device insertion tool, a normal force to two or more attachment points of a burr hole device component simultaneously.

In another example, a hand-held burr hole device insertion tool comprises a first end and a second end, the first end configured for simultaneous application of a normal force to two or more attachment points of a burr hole support clip.

The details of one or more examples are set forth in the accompanying drawings and the description below. Other features, objects, and advantages will be apparent from the description and drawings, and from the claims.

DETAILED DESCRIPTION

The present disclosure describes a burr hole device insertion tool and techniques for inserting a burr hole device component, such as a burr hole device support clip, using the burr hole device insertion tool. In some examples, the burr hole device insertion tool is configured to evenly distribute a pressure load to a support clip to fixate a support clip into the base of a burr hole cap assembly, the support clip fixating the lead (or catheter) in the burr hole cap assembly. Distributing a pressure load evenly to a support clip via the burr hole device insertion tool during delivery of the support clip to the cap assembly base may reduce lead and/or catheter misplacement and/or misalignment during cap assembly.

One or more electrical leads may be implanted in a brain of a patient, such as during a deep brain stimulation (DBS) procedure. Insertion tools may be used to during a DBS procedure to help with the implantation of the lead. During lead placement, it is desirable that the lead is placed and stays in the target location. A burr hole device, such as a burr hole cap assembly, is used to help fixate the DBS lead during implantation and throughout the life of implantation of the lead. A support clip may be a burr hole cap assembly component that may be used to fixate the lead. For example, a burr hole cap assembly base may be affixed to the patient's skull and positioned proximate to the burr hole. Once the one or more electrical leads are placed at the target location in the patient's brain through a hole in the burr hole cap assembly base, a support clip may be attached to the burr hole cap assembly base to fixate the lead (e.g., via a retention jaw of the support clip). An insertion tool may be used to deliver and attach the support clip to the base. In some examples, the support clip may be configured to be attached to the base via two or more attachment points, and the insertion tool may be used to apply a force to cause the attachment points to attach and/or interconnect with the base, e.g., the tool may be used to press on the support clip to cause the support clip to attach to the base.

It may be desirable for the lead(s) to be held substantially in place while a practitioner attaches the support clip to the base. If the practitioner struggles with attaching the support clip to the base, the leads may move from the target location, which may be undesirable. In some examples, a support clip with two or more attachment points may provide increased stability in fixating the support clip to the base (e.g., as compared to a support clip with a single attachment point), thereby increasing the ability of the support clip to reliably fixate the leads in the target location during the life of the implantation. However, it may be difficult to attach to the base without applying a relatively even force to each of the attachment points at the same time. Applying a force to the center of the clip in order to apply a relatively even force to each of the attachment points may not be an option because at least a portion of the retention jaw of the support clip may be in the center of the support clip, and applying a force to the center of the support clip by pressing on the portion of the retention jaw may damage or break the retention jaw. Applying a force to a single off-center position of the clip results in an uneven pressure applied to the two or more attachment points, which may cause a practitioner to struggle with attaching the support clip to the base. For example, an uneven pressure applied to the two or more attachment points may cause the support clip to shift, rotate, or tilt during application of the force. Therefore, it is desirable to apply a relatively even force to each of the attachment points at the same time to attach the support clip to the base.

In examples disclosed herein, a burr hole device insertion tool is configured to evenly distribute a pressure load to a support clip at two or more attachment points to fixate a support clip into the base of a burr hole cap assembly. The burr hole device insertion tool may be further configured to open and close the lead attachment mechanism of the support slip, e.g., a retention jaw. The burr hole device insertion tool may be configured to allow the user and/or physician an unobstructed view of the burr hole device, the support clip, and/or the leads during insertion and/or attachment of the support clip to the base.

Figure 1:
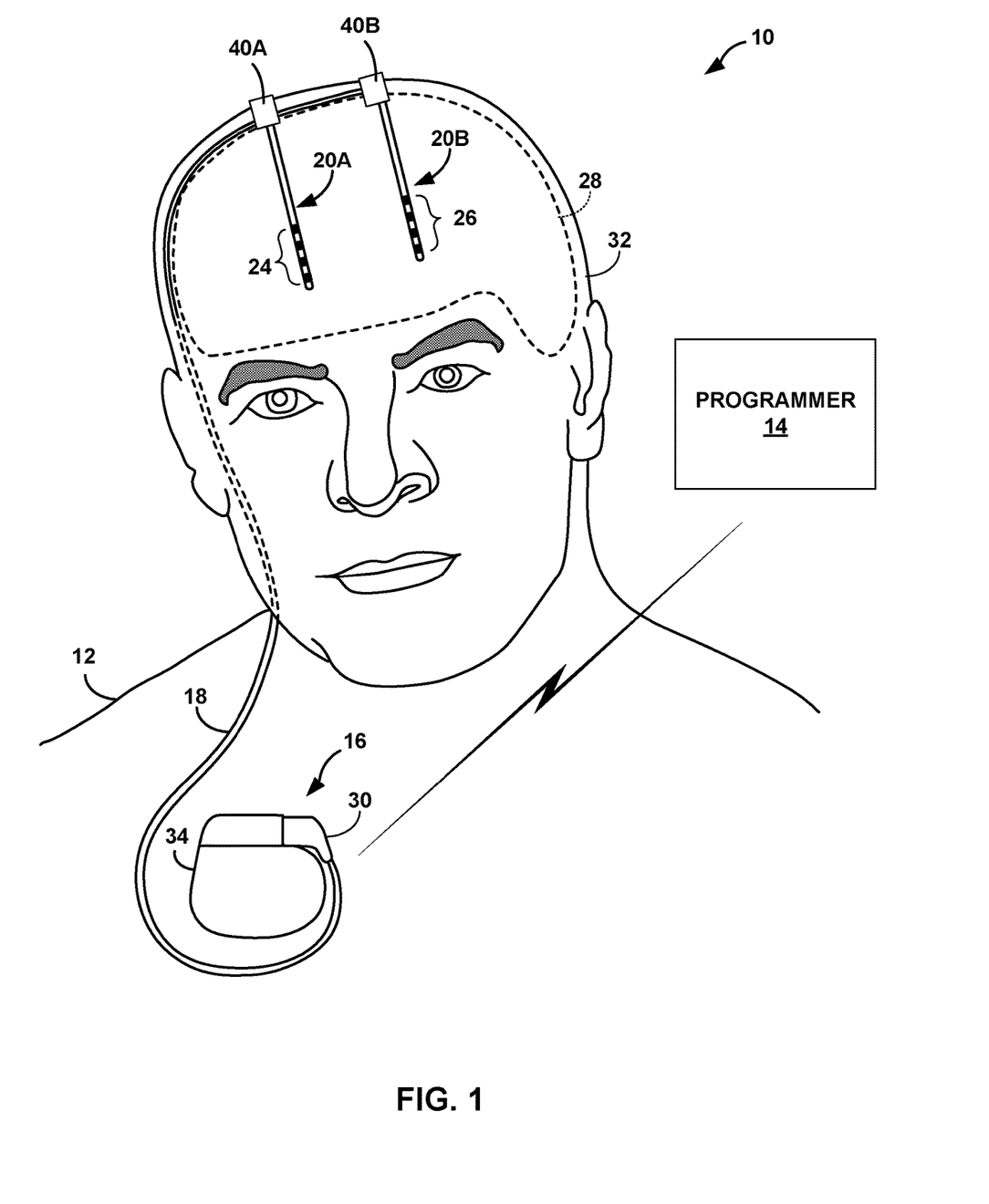
FIG. 1 is a conceptual diagram illustrating an example therapy system configured to deliver therapy to patient to manage a disorder of patient, in accordance with this disclosure.

FIG. 1 is a conceptual diagram illustrating an example therapy system 10 configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In some examples, leads 20 may be positioned to deliver therapy to a surface of brain 28 (e.g., the cortical surface of brain 28). For example, in some examples, IMD 16 may provide cortical stimulation therapy to patient 12. e.g., by delivering electrical stimulation to one or more tissue sites in the cortex of brain 28.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead 18 is coupled to IMD 16 via connector block 30 (also referred to as a header), which may include, for example, electrical contacts electrically coupling to respective electrical contacts on lead 18. The electrical contacts electrically couple the electrodes 24, 26 carried by leads 20 to IMD 16. Lead 18 traverses from the implant site of IMD 16 within a chest cavity of patient 12, along the neck of patient 12 and through the cranium of patient 12 to access brain 28. IMD 16 can be constructed of a biocompatible material resisting corrosion and degradation from bodily fluids. IMD 16 may comprise a hermetic housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 so electrodes 24, 26 can provide electrical stimulation to target therapy delivery sites within brain 28 during treatment. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MIDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus *ceruleus*, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

Although leads 20 are shown in FIG. 1 as being coupled to a common lead 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In this disclosure, when describing an electrode on housing 34, such disclosure may also apply to cases where housing 34, itself, performs the operation of an electrode. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, and, in the case of electrical stimulation pulses, pulse rate, pulse width, waveform shape, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals of patient 12. For example, IMD 16 may include sensing circuitry configured to sense bioelectrical brain signals within one or more regions of brain 28 via a subset of electrodes 24, 26, another set of electrodes (150 (FIG. 2), 206, 210 (FIG. 3), or both.

Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals (discussed in greater detail below). In some examples, the sensing circuitry of IMD 16 may sense bioelectrical brain signals via one or more of the electrodes 24, 26 also used to deliver electrical stimulation to brain 28. In other examples, one or more of electrodes 24, 26 may be used to sense bioelectrical brain signals while one or more different electrodes 24, 26 may be used to deliver electrical stimulation.

In accordance with one or more example techniques described in this disclosure, one or more burr hole cap assemblies 40A and 40B (collectively "burr hole cap assemblies 40") may be utilized to secure a position of one or both of leads 20A and 20B. Burr hole cap assemblies 40 may be affixed to skull 32 and cover one or more burr holes in skull 32 as well as fixate leads 20 such that electrodes 24, 26 stay in the target location during implantation of leads 20 and throughout the life of implantation of the lead, as illustrated and described below with reference to FIGS. 2-3. In some examples, burr hole cap assemblies 40 may include a base configured to be attached to skull 32, a support clip configured to attached to the base via two or more attachment points and to fixate one or more leads 20, and a cover configured to cover/cap/plug the burr hole. For example, a clinician and/or user may attach the base to skull 32, and a position and attach the support clip to the base using a burr hole device insertion tool, such as burr hole device insertion tool 400 illustrated and described below with reference to FIGS. 4-6. The burr hole device insertion tool may be configured to evenly distribute a pressure load to the support clip to fixate the support clip into the base via two or more attachment points. The burr hole device insertion tool may also include a retention jaw mating structure configured to mate with a receiving structure of the support clip retention jaw and thereby open and close the retention jaw to fixate and free leads 20, respectively.

External medical device programmer 14 is configured to wirelessly communicate with IMD 16 to provide or retrieve therapy information. Programmer 14 is an external computing device the user, e.g., the clinician and/or patient 12, may use to communicate with IMD 16. For example, programmer 14 may be a clinician programmer the clinician uses to communicate with IMD 16 and program one or more therapy programs for IMD 16. In addition, or instead, programmer 14 may be a patient programmer allowing patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) presenting information to the user. In addition, programmer 14 may include a touch screen display, keypad, buttons, a peripheral pointing device or another input mechanism allowing the user to navigate through the user interface of programmer 14 and provide input. If programmer 14 includes buttons and a keypad, the buttons may be dedicated to performing a certain function, e.g., a power button, the buttons and the keypad may be soft keys changing in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device running an application enabling the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs providing efficacious therapy to patient 12 to address symptoms associated with the patient condition. For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors generating signals indicative of motion of patient 12. Programmer 14 may assist the clinician in the creation/identification of therapy programs by providing a system for identifying potentially beneficial therapy parameter values.

In some examples, programmer 14 (or another computing device) is configured to determine, for at least one electrode (e.g., for each electrode 24, 26) of therapy system 10, a therapeutic window, and generate and display information regarding the determined therapeutic windows. For example, programmer 14 may generate a display listing each electrode 24, 26, or a subset of electrodes 24, 26, and, for each electrode, the respective therapeutic window. The therapeutic windows can be displayed as, for example, an efficacy threshold value and an adverse-effects threshold, which may define the boundaries of the therapeutic window in some examples (e.g., X to Y, or X-Y, where X and Y are values for a particular stimulation parameter, such as amplitude). In addition, or instead, the therapeutic windows can be displayed as a magnitude of the difference between the efficacy threshold value and the adverse-effects threshold (e.g., a single number indicating the difference between the efficacy threshold value and the adverse-effects threshold).

As discussed above, the therapeutic windows of electrodes 24, 26 may provide a basis for comparing the potential benefits of each of the electrodes. For example, an electrode associated with a relatively large therapeutic window may indicate the electrode will provide more latitude to find efficacious electrical stimulation parameter values for the patient than another electrode associated with a relatively small therapeutic window. In some examples, the therapeutic windows may be determined based on the actual implantation site of leads 20 within patient 12, i.e., post-operatively, so the information identifying the therapeutic windows for each of the electrodes 24, 26 may be specifically tailored to patient 12. As a result, the therapeutic windows may provide a useful basis for selecting electrode combinations for programming IMD 16.

In some examples, the therapeutic windows may be determined before leads 20 are implanted in patient 12. e.g., pre-operatively. For example, the therapeutic windows may be determined based on the expected implantation site of leads 20 in patient 12. In these examples, the therapeutic windows may be determined based on volume of tissue activation determined using images of patient 12 (e.g., based on a brain atlas specific to patient 12), so the information identifying the therapeutic windows for each of the electrodes 24, 26 may be specifically tailored to patient 12. The target location of leads 20 and electrodes 24, 26 may be selected and modeled, e.g., by a processor of programmer 14, in order to determine the VTAs expected to result from delivery of electrical stimulation by select electrode(s) 24, 26 of leads 20 if leads 20 were implanted in patient 12. In this way, the therapeutic windows may be used to determine at least some electrical stimulation parameter values pre-operatively, prior to implantation of leads 20. In addition, programmer 14 (or another device) may determine the therapeutic windows based on different target locations for electrodes 24, 26, e.g., in order to pre-operatively select an actual implant site for leads 20. Processor 14 may, for example, select the implant site resulting in the relatively largest therapeutic windows or the relatively greatest number of electrodes associated with therapeutic windows greater than or equal to a predetermined size.

Programmer 14 may also be configured for use by patient 12. When configured as a patient programmer, programmer 14 may have limited functionality (compared to a clinician programmer) in order to prevent patient 12 from altering certain functions of IMD 16 or applications detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system. Other combinations or components of system 10 may be possible. For example, rather than IMD 16, a system may include an external medical device coupled to leads similar to leads 24, 26.

During implantation of lead 16 within patient 12, a clinician may attempt to position electrodes 24, 26 of leads 20 close to or within a target anatomical region. The anatomical region within patient 12 serving as the target tissue site for stimulation delivered by IMD 16 may be selected based on the patient condition. For example, stimulating structures of brain 28, such as the Substantia Nigra, may help reduce the number and magnitude of tremors experienced by patient 12. Other anatomical regions for DBS may include the subthalamic nucleus, globus pallidus interna, ventral intermediate, and zona inserta.

With the aid of programmer 14 or another computing device, a clinician may select values for therapy parameters for therapy system 10, including an electrode combination. By selecting electrodes 24, 26 for delivering electrical stimulation therapy to patient 12, a clinician may modify the electrical stimulation therapy to target one or more regions of tissue (e.g., specific anatomical structures) within brain 28 and avoid other regions of tissue within brain 28. In addition, by selecting values for the other stimulation parameter values defining the electrical stimulation signal. e.g., the amplitude, pulse width, and pulse rate, the clinician may generate an efficacious therapy for patient 12 delivered via the selected electrode subset. Due to physiological diversity, condition differences, and inaccuracies in lead placement, the parameter values may vary between patients.

During a programming session, the clinician may determine one or more therapy programs providing effective therapy to patient 12. Patient 12 may provide feedback to the clinician as to the efficacy of the specific program being evaluated, which may include information regarding adverse effects of delivery of therapy according to the specific program Once the clinician has identified one or more programs beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

Figure 2:
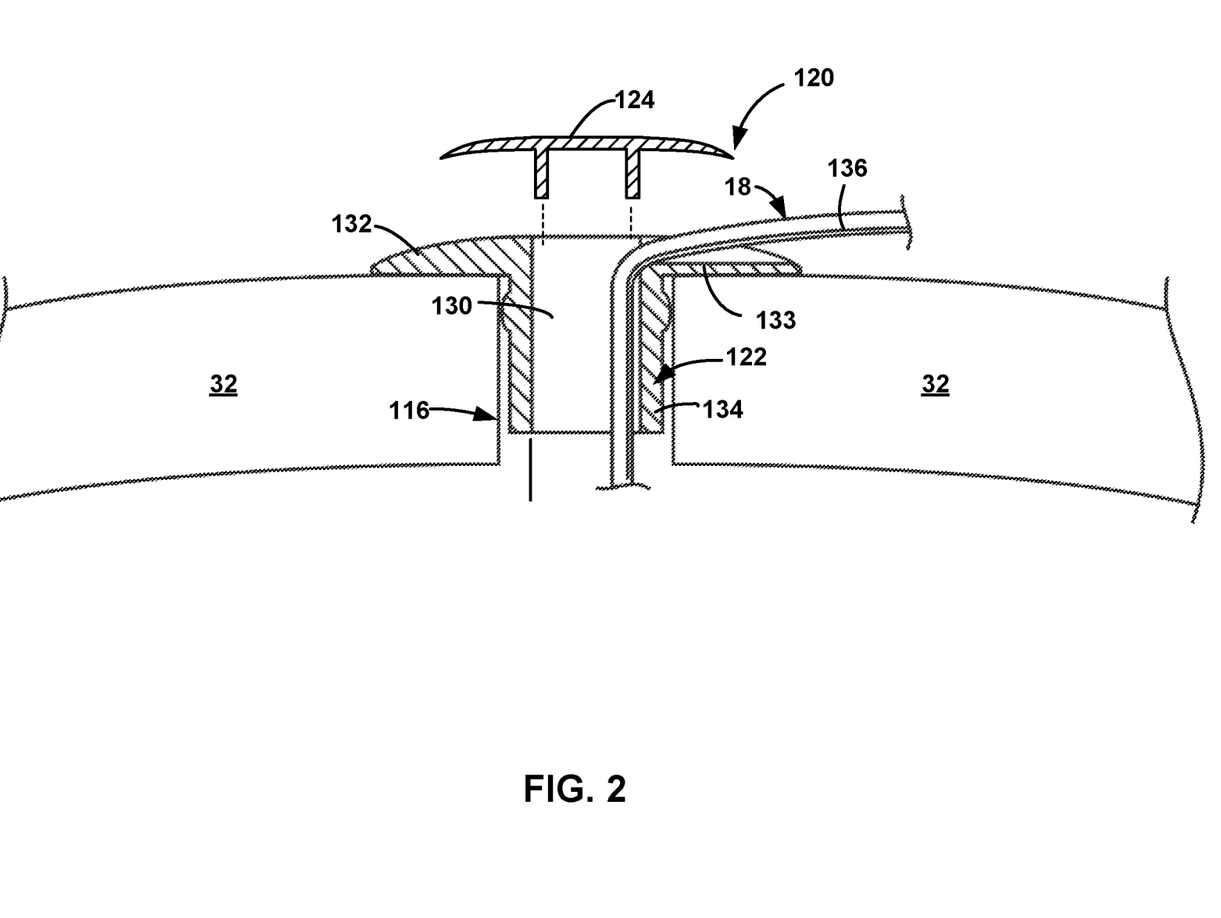
FIG. 2 is a schematic cross-sectional illustration of a lead extending through a base of a burr hole cap assembly inserted in a burr hole through a cranium of a patient, in accordance with this disclosure.

FIG. 2 is a schematic cross-sectional illustration of lead 18 extending through base 122 of burr hole cap assembly 120, where base 122 is positioned within burr hole 116 through cranium 32 of patient 12. The cross-section is taken through burr hole cap assembly 120, as well as through a center of therapy lead 18. As shown in FIG. 2, burr hole cap assembly 120 includes base 122, which defines opening 130, and cover 124, which is shown in FIG. 2 in a disassembled state, in which cover 24 is not mechanically coupled to base 122. Assembly lines are shown in FIG. 2 to illustrate how cover 24 may be aligned with base 22 such that it partially fits within opening 30 define by base 22 and substantially covers opening 30. Burr hole cap assembly 120 may also include a support clip (not shown) configured to retain lead 18 and attach lead 18 to burr hole cap assembly 120, such as support clip 216 described and illustrated below with reference to FIG. 3.

Opening 130 defined by base 122 is configured to receive therapy lead 18. In some examples, opening 130 has a circular cross-section, but other cross-sectional shapes (e.g., quadrilateral) are contemplated. In the example shown in FIG. 2, opening 130 is sized to receive lead 18.

Base 122 is configured to be inserted in burr hole 116 and may help protect edges of burr hole 116. Base 122 may have any suitable configuration. In the example shown in FIG. 2, base 122 includes flange 132 that radially extends from shaft 134. Flange 132 may be integrally formed with shaft 134 or may be physically separate from shaft 134 and mechanically coupled to shaft 134. Flange 132 is configured to engage with cranium 32 outside of burr hole 116 and shaft 134 is configured to engage with cranium 32 within burr hole 116. The intersection between flange 132 and shaft 134 may cover the edges of burr hole 116. The extension of flange 132 in a generally radially outward direction from shaft 134 helps to secure burr hole cap assembly 120 to an outer surface (i.e., the surface opposite the surface closest to the brain) of cranium 32.

In the example shown in FIG. 2, base 122 is configured such that lead 18 extends from a side of burr hole cap assembly 120, rather than from a top of burr hole cap assembly 120 (e.g., the surface furthest from cranium 32) when burr hole cap assembly 120 is placed in burr hole 116. In one example, flange 132 defines a plurality of grooves, including groove 133, which is configured to receive lead 18. Lead 18 may be configured to extend from burr hole cap assembly 120 through groove 133. Groove 133 may be, for example, a channel configured to guide lead 18 out of burr hole cap assembly 120. In some examples, flange 132 of base 122 defines a plurality of grooves, which may enable a clinician to select the point around base 122 that lead 18 exits burr hole cap assembly 120.

In other examples, burr hole cap assembly 120 is configured such that lead 18 exits burr hole cap assembly 120 from another surface of assembly 120, such as from a top of burr hole cap assembly 120. For example, cover 124 may define an opening that substantially aligns with opening 130 in base 122 when cover 124 is connected to base 122, and lead 18 may exit burr hole cap assembly 120 through the opening defined by cover 124. Other techniques for guiding lead 18 out of burr hole cap assembly 120 may be used.

Base 122 may be affixed to cranium 32 of patient 12 using any suitable technique, e.g., by suturing or via set screws. For example, base 122 may define apertures configured to receive one or more sutures or set screws. In some examples, at least a portion of base 122 may be formed from a compressible material, such that shaft 134 of base 122 may be sized to accommodate a predetermined range of burr hole sizes. In other examples, base 122 is sized specifically for one burr hole size.

Cover 124 is configured to be mechanically connected to base 122 and substantially cover (e.g., plug) opening 130 defined by base 122. In this way, cover 124 may substantially cover burr hole 116. In the example shown in FIG. 2, cover 124 is configured to cover groove 133 (as well as the other grooves 133), such that when cover 124 is mechanically connected to base 122, lead 18 extends from burr hole cap assembly 120 through a relatively small opening defined between base 122 and cover 124. In some examples, lead 18 is fixed substantially in place by a support clip, e.g., support clip 216 of FIG. 3.

Lead 18 may be introduced into patient 12 using any suitable technique. In some examples, a distal end of lead 18 may be guided to a target tissue site within patient 12 (e.g., within the brain of patient 12) with the aid of a stereotactic instrument, which may permit precise movement of lead 18 within brain 28. In some of these examples, a support clip is configured to be attached to bass 122 via two or more attachment points while lead 18 is still retained by the stereotactic instrument and held in place relative to the target tissue site via the stereotactic instrument. Once installed, a retention jaw of the support clip may be closed to substantially fix lead 18 in place relative to burr hole 116 and lead 18 may be released from the stereotactic instrument. For example, a clinician and/or user may position and attach the support clip to base 122 using a burr hole device insertion tool, such as burr hole device insertion tool 400 illustrated and described below with reference to FIGS. 4-6. As mentioned above, the burr hole device insertion tool may be configured to evenly distribute a pressure load to the support clip to fixate the support clip into the base via two or more attachment points. The burr hole device insertion tool may also include a retention jaw mating structure configured to mate with a receiving structure of the support clip retention jaw and thereby open and close the retention jaw to fixate and free lead 18, respectively.

Figure 3:
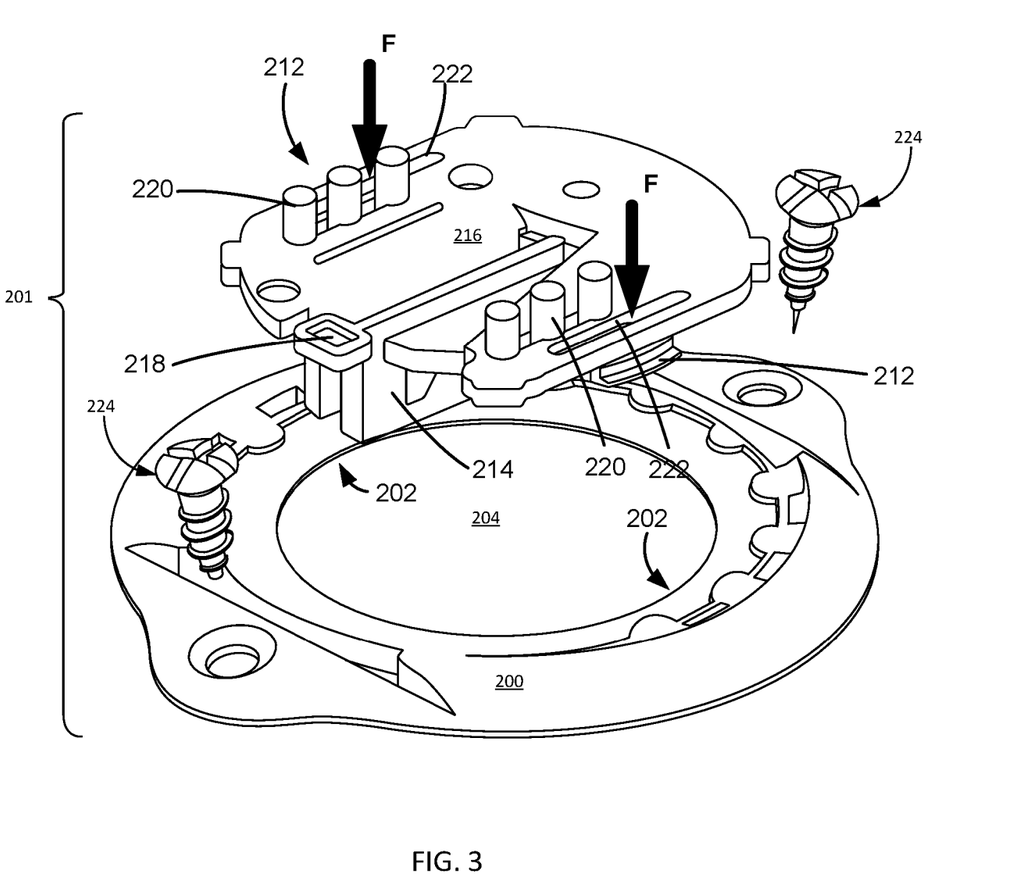
FIG. 3 is an exploded conceptual illustration of a burr cap cover assembly configured to be inserted in a burr hole in a cranium of a patient, in accordance with this disclosure.

FIG. 3 is an exploded conceptual illustration of a burr hole cap assembly 201 configured to be inserted in a burr hole in a cranium of a patient, in accordance with this disclosure. In the example shown, burr hole cap assembly 201 includes base 200, support clip 216, and cover 208.

In the example shown, base 200 is attached to cranium 32, e.g., via screws 224. In some examples, base 200 may be attached to cranium 32 via any other method, e.g., an adhesive. Base 200 may be configured to cover burr hole 116 in cranium 32 of a patient 12. Base 200 may define an opening 204 configured to receive leads 18 and/or 20. In the example shown, base 200 includes one or more attachment receivers 202. Attachment receivers 202 may be configured to attachment points 212 of support clip 216. In some examples, attachment receivers 202 may comprise two or more recesses around base 200 defining hole 204, a single recess around the entire circumference of base 200 defining hole 204, or any other suitable receiver for mating and/or engaging with attachment points 212.

In the example shown, support clip 216 is configured to be attached to base 200 via two or more attachment points 212. In some examples, attachment point 212 may be protrusions of support clip 216 such as tabs as illustrated in FIG. 3. In other examples, attachment points may be a protrusion or any other suitable means for mating with and/or engaging attachment receivers 202. Attachment points 212 may be configured to be mated with and/or engaged with attachment receivers 202 via application of a force and/or pressure to attachment points 212 in a direction towards base 200, e.g., a force F normal to a plane defined by opening 204. The force may cause attachment points 212 to press into bass 200 proximate to the edge of base 200 defining opening 204. Attachment points 212 may be shaped such that the downward pressure causes the attachment points to flex inwards towards the center of support clip 216, allowing attachment points 212 to be pressed downward into opening 204. In the example shown, recesses 222 in support clip 216 may be configured to allow attachment points 212 to flex inwards. Once flexed and pressed into opening 204 along the edge of base 200, attachment points 212 may have a lip that may slide into attachment receivers 202 via an outward force on attachment points 212 resisting the inward flexing of the attachment points 212, e.g., a lip on the tabs as illustrated in FIG. 3 may slide into a recess under the inner edge of base 200 defining opening 204. Although FIG. 3 illustrates two attachment points 212 and two attachment receivers 202, base 200 may include more than two attachment receivers 212 and support clip 216 may include more than two attachment points 212. In some examples, base 200 may include the two or more attachment points 212 and support clip may include corresponding two or more attachment receivers 202, e.g., recesses. In some examples, both base 200 and support clip 216 may include two or more attachment points 212 and attachment receivers 202 configured to mate and/or engage so as to affix support clip to base 200.

In the example shown, support clip 216 includes retention jaw 214. Retention jaw 214 may be configured to fixate and/or retain leads 18 and/or 20 in a closed position, and free leads 18 and or 20 in an open position. Support clip 216 may include locking structures, e.g. protrusions and/or recesses configured to engage with recesses and/or protrusions of retention jaw 214 so as to hold retention jaw 214 in an open or closed position. Retention jaw 214 may include retention jaw receiving structure 218, e.g., a recess, which may be configured to mate and/or engage with a retention jaw mating structure to open and close the retention jaw. For example, burr hole device insertion tool 400 may include a retention jaw mating structure, as illustrated and described with reference to FIG. 6, which may be positioned within retention jaw receiving structure 218. A user may push retention jaw 214 down, e.g., towards base 200, to disengage the one or more locking structures to free retention jaw 214 to be moved from the open and/or closed position to the opposite closed and/or open position, and the user may then apply a lateral force to retention jaw 214 via burr hole device insertion tool 400 engaged with retention jaw receiving structure 218 to open and/or close retention jaw 214.

In the example shown, support clip 216 includes a plurality of posts 220. In some examples, posts 220 may be configured to interference and/or friction fit with two or prongs of burr hole device insertion tool 400.

Support clip 216 may be made of plastic, metal, or any suitable material configured to allow support clip 216 to be attached to base 200 via two or more attachment points with the application of a substantially even pressure or force applied to the two or more attachment points.

Figure 4A:
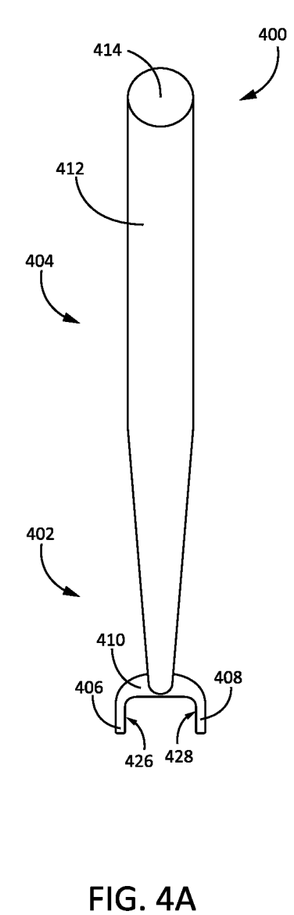
FIG. 4A is a conceptual illustration of a front view of a burr hole device insertion tool, in accordance with this disclosure.
Figure 4B:
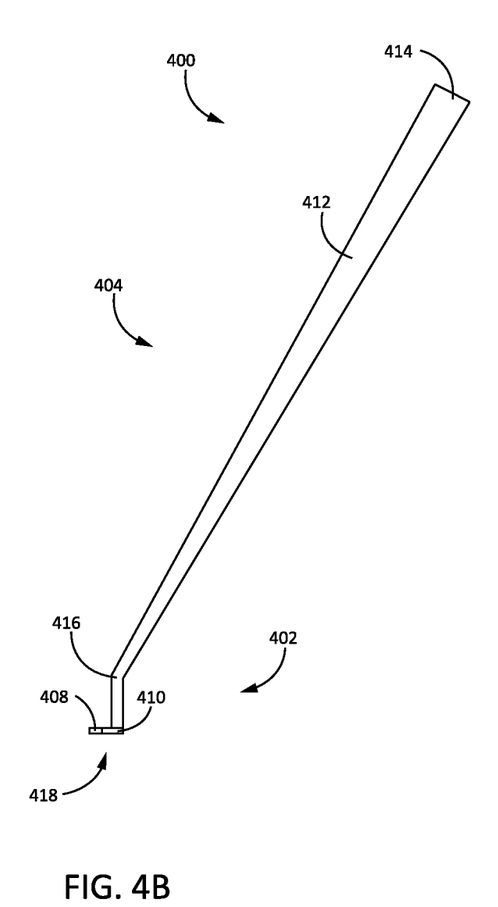
FIG. 4B is a conceptual illustration of a side view of a burr hole device insertion tool, in accordance with this disclosure.

FIGS. 4A and 4B are conceptual illustrations of different views of a burr hole device insertion tool 400 and are described together below. FIG. 4A is a conceptual illustration of a front view of a burr hole device insertion tool 400, in accordance with this disclosure. FIG. 4B is a conceptual illustration of a side view of a burr hole device insertion tool, in accordance with this disclosure. In the examples shown, burr hole device insertion tool 400 includes a first end 402 configured for simultaneous application of a normal force to two or more attachment points of support clip 216, and a second end 404.

In the examples shown, first end 402 includes first engagement point 406, second engagement point 408, bend 416, and connector 410. In some examples, first engagement point 406 and second engagement point 408 may be prongs extending from connector 410 in substantially the same direction and each comprise a substantially planar bottom surface 418. First engagement point 406 and second engagement point 408 may be configured to slidably engage with, attach to, and/or detach from support clip 216 via an interference and/or friction fit to posts 220. Connector 410 may be configured to mechanically connect first engagement point 406 and second engagement point 408 to handle 412 and to allow a clear line of sight between a center of support clip 216 and a user of burr hole device insertion tool 400 during insertion of support clip 216 to base 200. For example, connector 410 may be U-shaped and in the same plane with first engagement point 406 and second engagement point 408. In some examples, the bottom surface of connector 410 may be substantially planar and co-planar with bottom surfaces 418 or first and second engagement points 406, 408.

In the examples shown, second end 404 includes handle 412 and end 414. Handle 412 may include bend 416, e.g., configured to allow a user of burr hole device insertion tool 400 a clear light of sight to a center of support clip 216. Handle 412 may be configured to be held and manipulated by hand by a user of burr hole device insertion tool 400. End 414 may include a retention jaw mating structure such as illustrated and described below with reference to FIG. 6.

Burr hole device insertion tool 400 may be made of plastic, metal, or any suitable material for a user to manipulate to apply a substantially even normal force and/or pressure to support clip 216.

Figure 5:
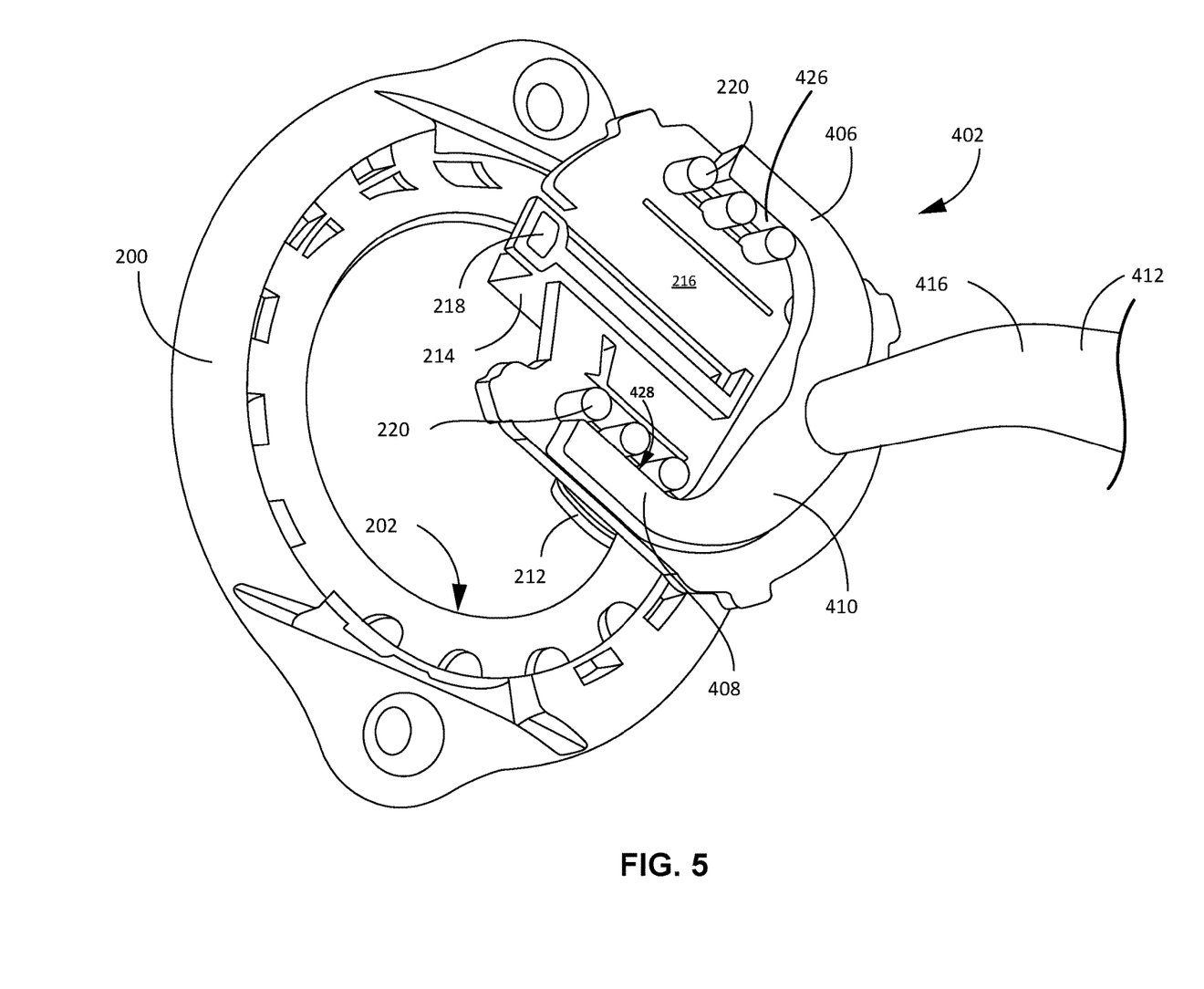
FIG. 5 is a conceptual illustration of a burr hole device insertion tool attached to a support clip, in accordance with this disclosure.

FIG. 5 is a conceptual illustration of a burr hole device insertion tool 400 attached to support clip 216, in accordance with this disclosure. In the example shown, first end 402 is slidably attached to support clip 216 via an interference and/or friction fit with posts 220. For example, the opposing surfaces 426, 428 of engagement points 406, 408 may be spaced so as to engage with, grip, and/or friction fit with posts 220 while bottom surface 418 may be in contact with a top surface of support clip 216 at or near attachment points 212. In some examples, the opposing surfaces 426, 428 of engagement points 406, 408 may be spaced by a distance substantially equal to 0.43 mm. First engagement point 406 and second engagement point 408 are substantially near attachment points 212 when slidably attached to support clip 216 and are positioned so as to apply a normal force to support clip 216 substantially evenly at the attachment points 212 via first engagement point 406 and second engagement point 408. A clinician and/or user may manipulate first end 402 via handle 412 and may have a clear line of sight to the center of support clip 216, e.g., to retention jaw 214, in order to insert leads 18 and/or 20 into an opening of retention jaw 214 in an open position while aligning support clip 216 to base 200. The clinician and/or user may then apply a downward force and/or pressure to engagement points 406, 408 via handle 412, which may then apply a downward force and/or pressure to attachment points 212 substantially evenly.

Figure 6:
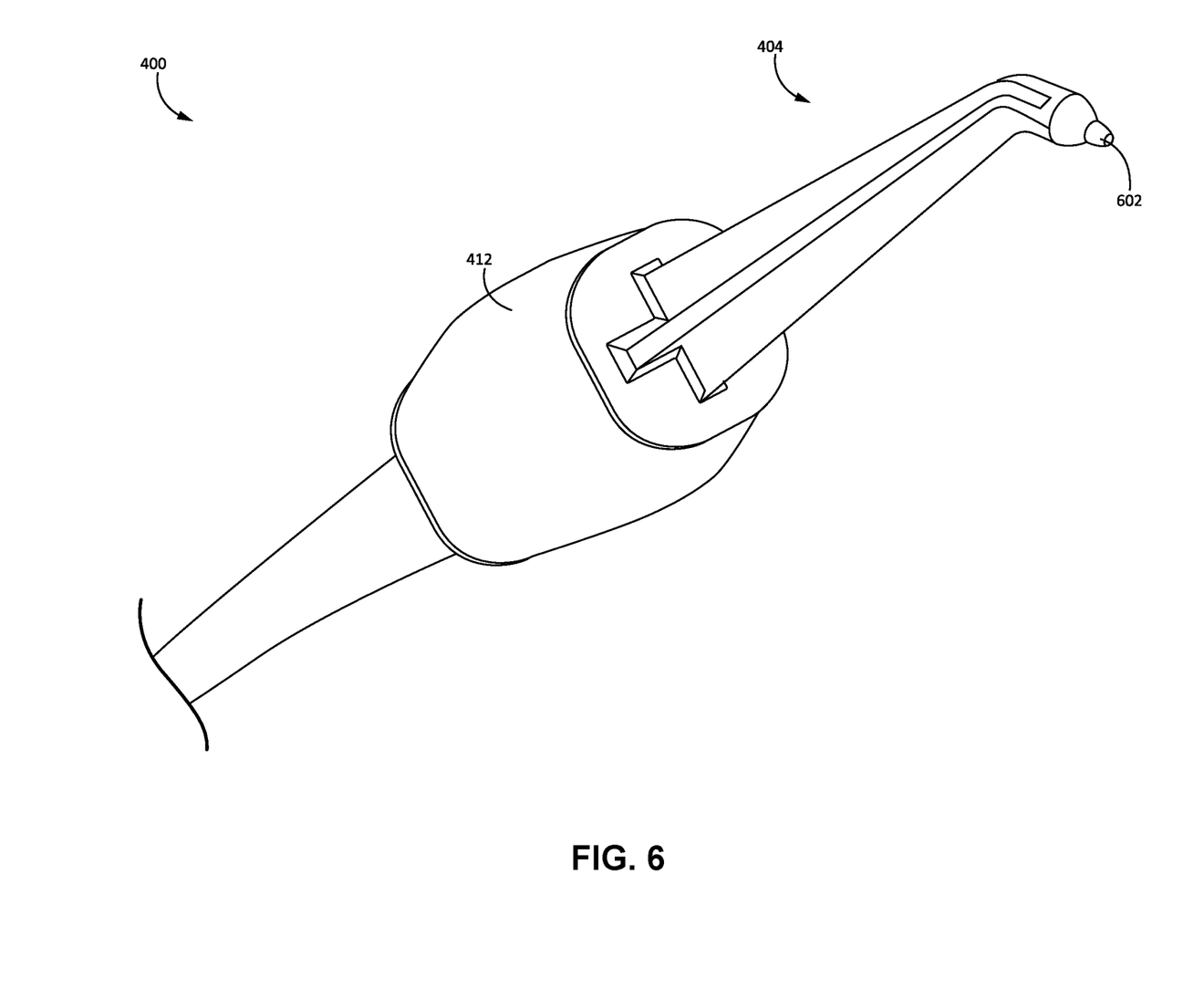
FIG. 6 is a conceptual illustration of a burr hole device insertion tool second end including a retention jaw mating structure, in accordance with this disclosure.

FIG. 6 is a conceptual illustration of a burr hole device insertion tool 400 second end 404 including a retention jaw mating structure 602, in accordance with this disclosure. In the example shown, retention jaw mating structure 602 is positioned at the distal end of handle 412. In some examples, retention jaw mating structure 602 may be located anywhere along handle 412 on anywhere on burr hole device insertion tool 400. In the example shown, retention jaw mating structure 602 has a spherical shape. In some examples, retention jaw receiving structure 218 may be a spherically shaped recess configured to engage with retention jaw mating structure 602. In other examples, other shapes are contemplated. For example, retention jaw mating structure 602 may have a cubic, polygon, or any other suitable shape, and retention jaw receiving structure 218 may be a correspondingly shaped recess configured to engage with retention jaw mating structure 602. Retention jaw mating structure 602 may be formed from burr hole device insertion tool 400, e.g., molded and/or shaped from the material of burr hole device insertion tool 400, or retention jaw mating structure 602 may be a separate structure, such as an endcap, attached to burr hole device insertion tool 400.

Figure 7:
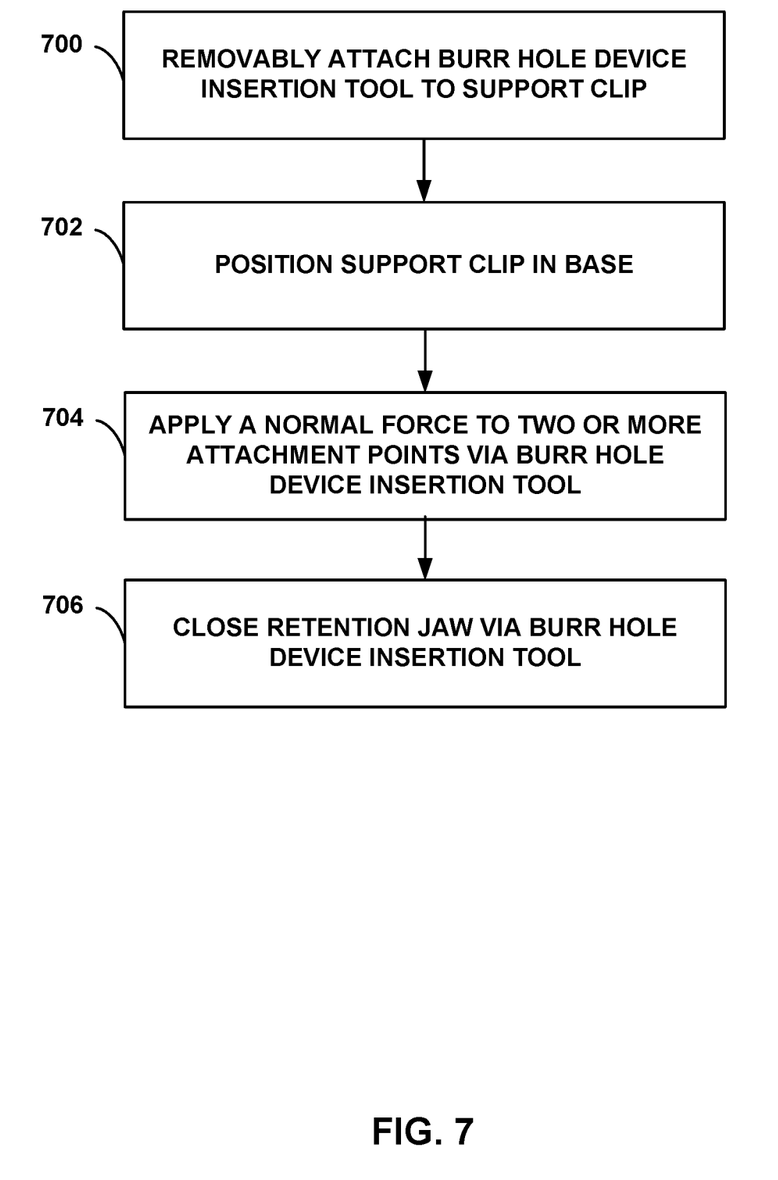
FIG. 7 is a flowchart of an example method of inserting a support clip into a base using a burr hole device insertion tool, in accordance with this disclosure.

FIG. 7 is a flowchart of an example method of inserting support clip 216 into base 200 using burr hole device insertion tool 400, in accordance with this disclosure. The example method is described with respect to burr hole device insertion tool 400 and burr hole cap assembly 201 of FIGS. 3-6.

A clinician and/or user may attach burr hole device insertion tool 400 to support clip 216 (700). For example, the clinician and/or user may attach first end 402 to support clip 216 by slidably attaching first engagement point 406 and second engagement point 408 to posts 220 via an interference and/or friction fit to posts 220. In some examples, first end 402 may attach to support clip 216 by any suitable means, e.g., via an adhesive, interlocking features of first end 402 that engage with corresponding features of support clip 216, an interference and/or friction fit with any other structural features of support clip 216, or any other suitable method. In some examples, bottom surfaces 418 of engagement points 406, 408 may be in contact with support clip 216 proximal to attachment points 212.

The clinician and/or user may position and/or align the two or more attachment points 212 of support clip 216 to at least one attachment receiver 202 of base 200 using burr hole device insertion tool 400 (702). For example, first end 402 and/or handle 412 of burr hole device insertion tool 400 may allow the clinician and/or user a clear line of sight to a center of support clip 216, and in some examples at least a portion of the edges of support clip 216 and a portion of base 200. The clinician and/or user may ensure that retention jaw 214 is in the open position, and may select a rotational orientation of support clip 216 within base 200, position leads 18 and/or leads 20 within retention jaw 214, and position support clip within base 200 such that attachment points 212 are in alignment with the at least one attachment receiver 202.

The clinician and/or user may apply a normal force to two or more attachment points 212 via burr hole device insertion tool 400 (704). For example, the clinician and/or or user may manipulate handle 412 to cause first end 202 to press and/or apply a substantially normal, e.g., downward, force on clip 216 towards base 200. The clinician and/or user may control, via handle 212 and connector 410, first engagement point 406 and second engagement point 408 to simultaneously apply a substantially even normal force to attachment points 212. In response to the simultaneous application of a normal force, attachment points 212 may mate with and/or engage with attachment receivers 202. For example, the force may cause attachment points 212 to press into base 200 proximate to the edge of base 200 defining opening 204. Attachment points 212 may be a part of and/or attached to support clip 216 proximate to recesses 222. The force may cause recesses 222 in support clip 216 to compress and allow attachment points 212 to flex inwards. Once flexed and pressed into opening 204 along the edge of base 200, attachment points 212 may have a lip that may slide into and/or mate with and/or engage with attachment receivers 202. For example, the compression of recesses 222 may cause an outward force on attachment points 212 that resists the inward flexing of the attachment points 212, e.g., a spring force, which may cause attachment points 212 to move outwards to engage with attachment recesses 202. In the example, first and second engagement points 406, 408 enable the clinician and/or user to apply the normal force simultaneously such that clip 216 does not, or is less likely to shift, rotate, or tilt during application of the force, and may thereby reduce and/or eliminating a cause of practitioner/user struggle in attaching clip 216 to base 200 and reduce lead and/or catheter misplacement and/or misalignment during cap assembly. Additionally, first and second engagement points 406, 408 enable application of a relatively even force to clip 216 without applying the force to the center of clip 216, e.g., at or near retention jaw 214.

Although FIG. 3 illustrates two attachment points 212 and two attachment receivers 202, base 200 may include one or more than two attachment receivers 202 and support clip 216 may include more than two attachment points 212. In some examples, the protrusions and recesses of clip 216 and base 200 may be switched, e.g., base 200 may include at least one protraction as attachment receivers 202 and the two or more attachment points 212 of support clip 216 may be recesses configured to engage the protrusions of base 200. In some examples, both base 200 and support clip 216 may include two or more attachment points 212 and attachment receivers 202 configured to mate and/or engage so as to affix support clip to base 200.

The clinician and/or user may close retention jaw 214 via burr hole device insertion tool 400 (706). For example, the clinician and/or user may detach first end 202 from support clip 216 after support clip 216 is attached to base 200. The clinician and/or user may then position and engage retention jaw mating structure 602 with retention jaw receiving structure 218. The clinician and/or user may then manipulate handle 212 to cause a normal force and/or a lateral force, simultaneously or in succession, to disengage retention jaw 214 for an open and/or closed position to close and/or open retention jaw 214. The clinician and/or user may manipulate handle 212 to cause a lateral force on retention jaw 214 via retention jaw mating structure 602 to close retention jaw 214, which may lock into a closed position via one or more locking structures and fixate leads 18 and/or leads 20. In the example, including retention jaw mating structure 602 with burr hole device insertion tool 400 adds convenience and reduces the time/effort a clinician and/or user needs to spend in both attaching clip 216 and closing retention jaw 214 to fixate leads 18 and/or leads 20. For example, the clinician and/or user may apply a normal force to two or more attachment points 212 via burr hole device insertion tool 400 to attach clip 216 to base 200, and then use burr hole device insertion tool 400 to lock retention jaw 214 to fixate leads 18 and/or 20, e.g., by flipping and/or reorienting burr hole device tool 400 between first end 402 and second end 404 and without switching tools. In other words, in the examples, burr hole device tool 400 may be used to improve clinician and/or user efficiency in two steps of the process of fixating leads 18 and/or 20, namely, attaching clip 216 to base 200 and fixating leads 18 and/or 20 via retention jaw 214 of clip 216.

Various examples of the disclosure have been described. Any combination of the described systems, operations, or functions is contemplated. These and other examples are within the scope of the following claims.

What is claimed is:

1. A system comprising:
a burr hole device component; and
a hand-held burr hole device insertion tool having a first end and a second end, the first end comprising two or more engagement points at a fixed distance from each other, the two or more engagement points configured for simultaneous application of a normal force to two or more attachment points of the burr hole device component to directly push the burr hole device component into a burr hole cap assembly base,
wherein the first end is further configured to slidably attach to, and detach from, the burr hole device component via an interference fit, and
wherein, when slidably attached, a bottom surface of the first end is in contact with a top surface of the burr hole device component near the two or more engagement points,
wherein the burr hole device component comprises a support clip configured to attach to the burr hole cap assembly base at the two or more attachment points, wherein the support clip is further configured to retain a lead that passes through the burr hole cap assembly base.

2. The system of claim 1, wherein the first end further comprises a connective element between the two or more engagement points, the connective element configured to allow a clear line of sight between a center of the burr hole device component and a user of the hand-held burr hole device insertion tool during insertion of the burr hole device component.

3. The system of claim 1, further comprising the burr hole cap assembly base.

4. The system of claim 3 further comprising:
a retention jaw mating structure configured to mate with a receiving structure of a retention jaw of the support clip to open and close the retention jaw.

5. The system of claim 4, wherein the second end comprises the retention jaw mating structure.

6. The system of claim 5, wherein the two or more attachment points comprise protrusions of the support clip, wherein the burr hole cap assembly base includes at least one recess configured to mate with the protrusions and secure the support clip to the burr hole cap assembly base.

7. The system of claim 6, wherein at least a portion of the support clip is configured to flex upon application of the normal force such that the protrusions can mate with the at least one recess.

8. The system of claim 1, wherein the first end and the second end are connected by a handle comprising a bend configured to allow a user of the hand-held burr hole device insertion tool a clear line of sight to a center of the burr hole device component.

9. The hand-held burr hole device insertion tool of claim 8, wherein the bend is such that the handle extends from the first end at an angle.

10. A method comprising:
applying, via a hand-held burr hole device insertion tool, a normal force to two or more attachment points of a burr hole device component simultaneously to directly push the burr hole device component into a burr hole cap assembly base,
wherein the hand-held burr hole device insertion tool comprises a first end and a second end, the first end comprising two or more engagement points at a fixed distance from each other, the two or more engagement points configured for simultaneous application of the normal force;
attaching the first end of the hand-held burr hole device insertion tool to the burr hole device component via an interference fit prior to applying the normal force, wherein, when attached, a bottom surface of the first end is in contact with a top surface of the burr hole device component near the two or more engagement points; and
aligning, via the hand-held burr hole device insertion tool, the two or more attachment points of the burr hole device component to a burr hole cap assembly base configured to receive the two or more attachment points.

11. The method of claim 10, wherein the burr hole device component is a support clip configured to attach to the burr hole cap assembly base at the two or more attachment points, wherein the support clip is further configured to retain a lead that passes through the burr hole cap assembly base.

12. The method of claim 11, wherein the two or more attachment points comprise protrusions of the support clip, wherein the burr hole cap assembly base includes at least one recess configured to mate with the protrusions and secure the support clip to the burr hole cap assembly base, wherein at least a portion of the support clip is configured to flex upon application of the normal force such that the protrusions can mate with the at least one recess.

13. The method of claim 11, further comprising:
closing, via the hand-held burr hole device insertion tool, a retention jaw of the support clip configured to retain the lead when closed, wherein the hand-held burr hole device insertion tool includes a retention jaw mating structure configured to mate with a receiving structure of the retention jaw of the support clip to open and close the retention jaw.

14. The method of claim 10, wherein the first end comprises:
a connective element between the two or more engagement points and configured to allow a clear line of sight between a center of the burr hole device component and a user of the burr hole device insertion tool during aligning of the two or more attachment points of the burr hole device component and applying the normal force to the two or more attachment points of the burr hole device component.

15. A hand-held burr hole device insertion tool comprising:
a first end and a second end, the first end comprising two or more engagement points at a fixed distance from each other, the two or more engagement points configured for simultaneous application of a normal force to two or more attachment points of a burr hole support clip to directly push the burr hole support clip into a burr hole cap assembly base,
wherein the first end and the second end are connected by a handle comprising a bend such that the first end extends from the handle at an oblique angle configured to allow a user of the hand-held burr hole device insertion tool a clear line of sight to a center of the burr hole support clip,
wherein the first end comprises two or more prongs configured to slidably attach to, and detach from, the burr hole support clip via an interference fit,
wherein, when slidably attached, a bottom surface of the first end is in contact with a top surface of the burr hole support clip near the two or more engagement points, and
wherein the second end comprises a retention jaw mating structure configured to mate with a receiving structure of a retention jaw of the support clip to open and close the retention jaw.

16. The hand-held burr hole device insertion tool of claim 15, wherein each of the two or more prongs are configured to simultaneously apply force to the burr hole support clip,
wherein the first end comprises a connective element between the two or more points configured to allow a clear line of sight between a center of the burr hole support clip and a user of the hand-held burr hole device insertion tool.

17. The hand-held burr hole device insertion tool of claim 16, wherein the two or more prongs and the connective element form a U-shape.

18. The hand-held burr hole device insertion tool of claim 15, wherein a surface of the two or more prongs is configured to simultaneously apply force to the burr hole support clip force is planar where the two or more prongs contact the burr hole support clip.

* * * * *